United States Patent [19]

Russenberger

[11] 4,149,406
[45] Apr. 17, 1979

[54] METHOD AND APPARATUS FOR DETERMINING THE TIME DEPENDENCY OF THE LENGTH OF A FISSURE IN A TEST SPECIMEN DURING A FRACTURE TEST

[76] Inventor: Max E. Russenberger, Kesselstrasse 10, 8200 Schaffhausen, Switzerland

[21] Appl. No.: 846,910

[22] Filed: Oct. 31, 1977

[51] Int. Cl.$^2$ ............................................. G01N 3/24
[52] U.S. Cl. ........................................ 73/775; 73/799
[58] Field of Search ................ 73/96, 88 R, 91; 338/2

[56] References Cited

U.S. PATENT DOCUMENTS

| 3,136,154 | 6/1964 | Christensen | 73/88 R |
| 3,596,269 | 7/1971 | Laska | 73/91 |

Primary Examiner—Anthony V. Ciarlante
Attorney, Agent, or Firm—Werner W. Kleeman

[57] ABSTRACT

A method of, and apparatus for, determining the time dependency of the length of a fissure in a test specimen during a fracture test which comprises securing an electrically conductive, areal or surface-like element to the test specimen such that during the fracture test it tears at the region of the fissure. An electrical parameter, such as the electrical resistance is determined between two measuring locations of the element. The measuring locations are selected such that the measurement current between such measuring locations passes through the region of the fissure. The element which is employed has a compact measuring section which is free of openings and the element is secured at the test specimen in such a manner that the measuring section completely covers the surface region which is occupied, during the fracture test, by the fissure until the end of the measurement of the length of the fissure, so that the resistance substantially uniformly increases with the length of the fissure.

13 Claims, 6 Drawing Figures

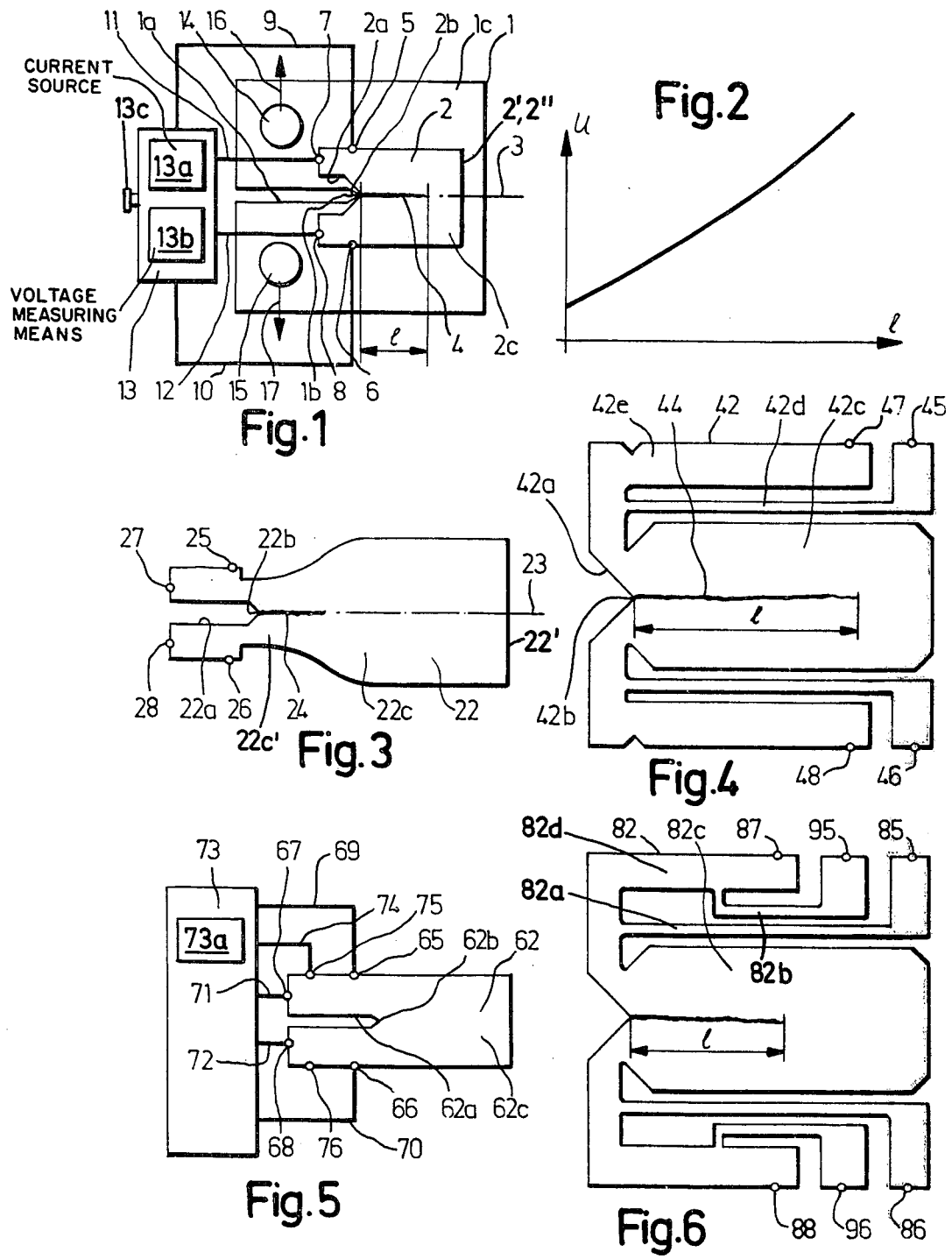

METHOD AND APPARATUS FOR DETERMINING THE TIME DEPENDENCY OF THE LENGTH OF A FISSURE IN A TEST SPECIMEN DURING A FRACTURE TEST

BACKGROUND OF THE INVENTION

The present invention relates to a new and improved method of, and apparatus for, the determination of the time dependency of the length of a fissure or crack in a test specimen or piece during a fracture test, wherein an electrically conductive, areal or surface-like element is attached in an insulated fashion at the test specimen such that it likewise tears at the region of the fissure during the fracture test, and wherein there is determined the electrical resistance between two measuring locations of the element, the measuring locations being selected in such a manner that the measuring current travels between the measuring locations through the region of the fissure, so that the resistance increases as a function of the length of the fissure.

During the determination of the breaking or rupture strength, for instance the tear strength of materials, there is oftentimes present the problem of measuring the length of the fissure or fracture which is forming in the test specimen during the entire fracture test. A state-of-the-art method employs for this purpose an electrically conductive element which however is insulated at one side. This element possesses a number of juxtapositioned, parallely extending, conductive strips which at least at both ends thereof are all conductively connected with one another. Prior to carrying out the actual fracture test, the element is bonded to the test specimen in such a manner that the strips extend transversely over the line at which later there is formed the fissure or crack. The element is connected at both sides of the fissure line with a measuring device for measuring the resistance. If a fissure is formed in the test body during the fracture test, then the strips of the element are also successively torn. Upon breakage of each strip, the resistance of the element is somewhat increased in stages. This resistance then constitutes a measure for the length of the fissure or crack.

This prior art method is associated with the drawback that the fissure length can only be discontinuously measured, and the resolution of the length is determined by the spacing of two neighboring strips. This spacing cannot be chosen to be randomly small, since otherwise the element no longer can be successfully bonded to the test specimen or body. Hence, the measurement, at best, can be accomplished with an accuracy of several tenths of a millimeter. This is then especially disturbing if it is desired to control the force exerted by the testing machine upon the test specimen as a function of the fissure length.

SUMMARY OF THE INVENTION

Hence, it is a primary object of the present invention to provide a new and improved method of, and apparatus for, accomplishing a continuous, uniform measurement of the fissure length of a test body or specimen.

Another and more specific object of the present invention aims at the provision of an improved method of, and apparatus for, reliably, accurately and simply determining the time dependency of the length of a fissure in a test specimen during a fracture test in a continuous manner.

Still a further significant object of this invention relates to a new and improved construction of apparatus for carrying out a continuous, uniform measurement of the fissure length of a test specimen, which apparatus is relatively simple in construction and design, economical to manufacture, easy to use, highly reliable in operation, not readily subject to breakdown or malfunction, and requires a minimum of maintenance and servicing.

Now in order to implement these and still further objects of the invention, which will become more readily apparent as the description proceeds, the method aspects of the present development are manifested by the features that there is employed an element having a compact, measuring section which is free of openings, the element is attached to the test specimen in such a manner that the measuring section completely covers the surface region which, during the fracture test, is occupied by the fissure or crack until the termination of the fissure length measurement, so that the resistance uniformly increases with the length of the fissure or crack.

Not only is the invention concerned with the aforementioned method aspects, but also relates to apparatus for the performance thereof with the aid of an electrically conductive, areal or surface-like element which is insulated at one side or face and intended to be secured to a surface of the test specimen or body. This element had a measuring section which is to be placed upon the test specimen at the region of the fissure. A measuring device serves to determine the electrical resistance between two measuring locations of the measuring section. Furthermore, the measuring section is compact and free of openings, so that the element can be attached to the test specimen in such a manner that the measuring section completely covers the surface region of the test body which is thereafter occupied by the fissure.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a top plan view of a test specimen or body and an element secured thereto as well as a schematically shown measuring device;

FIG. 2 is a graph showing the dependency of the voltage between the measuring locations as a function of the fissure or tear length;

FIG. 3 illustrates a variant construction of an element for obtaining a linear dependency between the fissure or tear length and the voltage;

FIG. 4 illustrates a variant of an element having four tongues or flaps for connection of the measuring device;

FIG. 5 illustrates an element together with a measuring device for carrying out a test method wherein the measuring current is regulated by maintaining constant the potential drop between two locations of the element; and FIG. 6 illustrates a further constuction of the element used in the practice of the method of the invention.

DETAILED DESCRIPTION OF THE PREFERRED EMBODIMENTS

Describing now the drawings, in FIG. 1 there is shown a test specimen or body 1 which for instance is formed of metal. Such is equipped with a notch 1a which extends along the plane of symmetry of the test specimen 1 and the inner end of which tapers and runs out into an edge 1b. Secured to the surface 1c of the test specimen 1 is an areal or surface-like element 2, attachment being accomplished for instance by adhesive bonding. This substantially flat element 2 is formed of a foil having two layers, merely generally indicated by reference characters 2', 2''. The layer 2' which bears upon the test specimen 1 consists of an electrically insulating plastic and possesses a thickness in the order of magnitude of 0.05 mm. At the side facing away from the test specimen 1 the element 2 has an electrically conductive layer 2''. This preferably consists of a rolled metal having a large specific resistance, for instance formed of constantan, and possesses a thickness of for instance 0.005 mm. The conductive layer 2'' is insulated with respect to the test specimen 1 by the plastic layer 2'. The element 2 is symmetrical with regard to the plane of symmetry 3, which also forms the symmetry plane of the test specimen 1. The element 2 is provided with a cut-out or notch 2a which is likewise symmetrical with regard to the symmetry plane 3, and the inner end of the notch 2a runs out into a tip 2b. This tip 2b is located in the symmetry plane 3 and coincides with the edge 1b of the notch 1a of the test specimen 1. The part of the element 2 which is located at the right of the tip 2b of the showing of FIG. 1 forms the measuring section 2c of such element 2. This measuring section 2c, during carrying out of the fracture test, completely covers the region of the test specimen-surface 1c which is occupied by the fissure or crack 4.

At both sides of the cut-out or notch 2a there is attached to the conductive layer 2'' of the element 2 at each respective one of the measuring locations 5 and 6 a conductor 9 and 10, respectively, for instance by welding or soldering. Further, there is conductively connected with the conductive layer of the element 2 at each side of the cut-out or notch 2a at a supply location 7 and 8 a conductor 11 and 12, respectively. The other ends of the conductors or lines 9, 10, 11 and 12 are connected with a measuring device 13. Such measuring device contains a constant current source, generally indicated by reference character 13a, in order to deliver a constant current to the element 2 by means of the conductors 11 and 12. This current flows along a current path from the supply location 7 to the supply location 8 or vice versa. Furthermore, the measuring device 13 contains means in order to measure the voltage between both of the measuring locations 5 and 6 and to either indicate and/or continuously register such, and such means have been indicated by reference character 13b. The measuring device 13 can thus contain for instance a milli-voltmeter or a voltage recorder. Moreover, the measuring device 13 of course can comprise spatially separated partial devices, of which for instance the one contains the constant current source and the other the means for the voltage indication.

Now to perform a fracture test the element 2 is initially bonded in the described manner with the test specimen 1 which is to be tested. Then the test specimen or body 1 is attached to the schematically illustrated holders 14 and 15 of a testing machine, for instance a tensile strength-testing machine. Further, the element 2 is connected by means of the conductors or lines 9, 10, 11 and 12 in the described manner with the measuring device 13. Thereafter, the test specimen 1 has applied thereto, by means of the testing machine, the forces which engage at the holders 14 and 15, these forces having been schematically indicated by the arrows 16 and 17.

Now in the test specimen 1 there is formed a fissure or crack 4 which starts at the edge 1b of the notch 1a and with time propagates along the plane of symmetry 3. The same fissure also is formed in the element 2. The measuring or measurement current which is generated by the constant current source 13a of measuring device 13 then flows from the one measuring location, for instance the measuring location 7, along a current path and past the measuring location 5 and around the fissure 4 and past the other measuring location 6 to the supply location 8. In the conductive layer 2'' of element 2 there is thus produced a surface-like current and potential distribution. In accordance with the theory of electrical conductors the potential equation of Laplace must be fulfilled, i.e., the sum of the second partial derivative of the potential after the space coordinates must disappear at each internal point. At the region of the fissure the equipotential lines extend from the fissure to the outer edge of the measuring section 2c. The equipotential lines starting at the measuring locations 5 and 6 extend to the cut-out or notch 2a. It is possible to designate both of these equipotential lines as measuring-equipotential lines, the course of which changes somewhat as the length of the fissure or crack increases. During the measurement the entire measuring current flows over both of the measuring-equipotential lines about the fissure. Now when the fissure grows as a function of time, then the resistance along the current path between the two measuring locations 5 and 6, or stated more exactly, between the two measuring-equipotential lines, uniformly increases with the fissure length. Since there is supplied a constant measuring current the voltage U between both of the measuring locations increases proportional to the resistance.

FIG. 2 shows the dependency of the voltage U between both of the measuring locations 5 and 6 as a function of the length 1 of the fissure 4. By measuring the voltage it is also possible to continuously and uniformly determine the length of the fissure 4 which increases as a function of time. The measuring current can be, for instance, in the order of about 0.1 amperes. The voltage U increases, for instance, by about 100 mV when the length of the fissure increases from null to a predetermined maximum value of about 5 mm. Tests have shown that the fissure length can be readily measured with an accuracy of 0.01 mm. It is here still mentioned that the fissure length of course only can be measured for such length of time as the fissure is located at the region of the element 2 and the fissure length is smaller than the predetermined maximum value. The heat which is developed during the measurement operation is removed by the test specimen 1 as well as the ambient air.

Of course it is possible to test test specimens of different sizes, and for this purpose there can be provided different size elements 2. The measuring device 13 is advantageously equipped with an adjustment element 13c which renders it possible to set the current intensity in accordance with the size of the element 2.

With the constructional embodiment of measuring element 2 which has been shown by way of example in FIG. 1, the resistance and the voltage U do not increase exactly linearly with the fissure length 1. This is so because with increasing fissure length not only does there increase the length of the current path, but also the cross-section between the end of the fissure and the right edge of the element 2 decreases. In FIG. 3 there is shown an element 22 where the resistance linearly increases with the length of the fissure 24. The element 22 is symmetrical with regard to the symmetry plane 23 and possesses a cut-out or notch 22a which runs out at the base thereof into a tip 22b located in the symmetry plane 23. At the right side of the notch 22a there is located the measuring section 22c. This measuring section 22c widens at least at a partial section 22c' which merges with the tip 22b in the direction of its edge 22' which faces away from the cut-out or notch 22a. The measuring locations 25 and 26 as well as the supply locations 27 and 28 which are separated therefrom, are arranged to the left of the widening partial section 22c' to both sides of the cut-out or notch 22a. The voltage and the resistance, respectively, are thus measured along a current path which extends from the one measuring location through the widening partial section 22c' of the measuring section 22c about the fissure or crack 24. By suitably accommodating the outline of the element 22 to the position of the measuring locations 25 and 26 and the supply locations 27 and 28, it is possible, as already mentioned, to achieve the result that the resistance increases exactly linearly along the current path as a function of the tear or fissure length.

This objective can not only be obtained by the construction of the element and arrangement of the measuring locations and supply locations as illustrated in FIG. 3, but also by other constructions of the element and the arrangements of the measuring locations and supply locations. For instance, the measuring locations and/or supply locations can also be of areal or surface-like construction, so that they extend for instance over the entire width of the flaps or tongues formed by the cut-out or notch 22a. In the conductive layer of the element 22 there prevails, for each tear or fissure length a certain potential distribution, which fulfills the previously discussed differential equation. Basically it is also possible to determine the configuration of the element 22 needed for obtaining a linear correlation. A purely mathematical method is, however, relatively complicated, so that advantageously there is initially determined mathematically an approximate solution and the exact outline or contour is then experimentally determined.

A linear correlation between the tear or fissure length and the resistance is then particularly advantageous when the voltage U which is proportional to the resistance is not only employed for indication or registration purposes, but is additionally utilized in order to control the testing machine, something which is advantageous for certain tests.

Now in FIG. 4 there is shown an element 42 having a substantially V-shaped cut-out or notch 42a, the tip of which has been designated by reference character 42b. The element 42 possesses a measuring section 42c at which there is present a fissure or crack 44 which begins at the tip 42b. At both lengthwise sides of the measuring section 42c the element 42 possesses a respective tongue or flap 42d as well as a tongue or flap 42e. At the free ends of the tongues 42d there are present the measuring locations 45 and 46 and at the free ends of the tongues 42e the supply locations 47 and 48. At the region of the cut-out or notch 42a the tongues 42d and 42e are joined to the measuring section 42c. During the measurement operation and in the ideal situation no current flows in the tongues 42d and practically only a current which is negligibly small in comparison to the current flowing the tongues or flaps 42e. Accordingly the potential in the entire tongues 42d has approximately the same value as at those locations of the measuring current path where the tongues 42d join with the tongues 42e. The element 42 differs from the element 2 particularly by virtue of the fact that it can be adhesively bonded to the test body or specimen in such a manner that the space between the holders 14 and 15 remain free and the conductors can be connected with the element at a relatively large distance from the holders.

Continuing, in FIG. 5 there is illustrated an element 62 having a cut-out or a notch 62a which terminates in a tip 62b and a measuring section 62c. The measuring locations have been designated by reference characters 65 and 66 and the supply locations by reference characters 67 and 68. A measuring device 73 is connected by means of the conductors or lines 69, 70, 71 and 72 with the measuring locations and supply locations, respectively. The measuring device 73 is furthermore connected by a conductor or line 74 with an intermediate location 75 of the element 62. This intermediate location 76 is located in the current path section between the measuring location 65 and the supply location 67. The measuring device 73 contains regulation means 73a in order to detect the potential drop between the intermediate location 75 and the measuring location 65 or the supply location 67 and for regulating the measuring current in such a manner that the aforementioned potential or voltage drop remains constant and thus also the measuring current. Of course instead of the foregoing there also can be detected the potential drop between the intermediate location 76 and one of the locations 66 or 68 and such utilized as the regulation voltage.

The element 82 illustrated in FIG. 6 is similarly constructed as the element 42, but however possesses three tongues 82a, 82b, 82d at each side of the measuring section 82c. The free ends thereof form the measuring locations 85 and 86, the supply locations 87 and 88, and the intermediate locations 95 and 96. The element 82 can be connected with a measuring device corresponding to the measuring device 73 shown in FIG. 5.

Finally, it is here further mentioned that of course still other forms or shapes of the elements are possible and that it would be also possible to measure the resistance in that, for instance, there is maintained constant the voltage between the measuring locations and instead there is measured the measuring current.

While there are shown and described present preferred embodiments of the invention, it is to be distinctly understood that the invention is not limited thereto, but may be otherwise variously embodied and practiced within the scope of the following claims. ACCORDINGLY,

What I claim is:

1. A method of determining the time dependency of the length of a fissure in a test specimen during a fracture test, comprising the steps of:
providing an electrically conductive, substantially flat element having a compact measuring section free of openings;
securing the element to the test specimen in a manner such that the measuring section completely covers a surface region which, during the fracture test, is occupied by the fissure until the end of the measurement of the length of the fissure, so that the resistance between two measuring locations of the element substantially uniformly increases with the length of the fissure;

carrying out a fracture test at the test specimen whereby the element tears at the region of the fissure of the test specimen; and measuring the length of the fissure formed.

2. The method as defined in claim 1, further including the steps of:

selecting the measuring locations such that the measuring current between the measuring locations passes through the element covering the region of the fissure.

3. The method as defined in claim 2, further including the steps of:

determining and coordinating the outline of the measuring section and the course of the current path relative to the fissure in such a manner that the resistance increases essentially linearly with the length of the fissure.

4. The method as defined in claim 3, further including the steps of:

utilizing an element having a measuring section which is symmetrical with respect to a plane of symmetry and which widens at least along a part of the symmetry plane towards one end thereof;

securing the element to the test specimen in such a manner that the fissure is essentially dispositioned at the plane of symmetry and increases in the direction of widening of the measuring section; and determining the current path such that the total measuring current must travel from the start of the fissure about the fissure.

5. The method as defined in claim 1, further including the steps of:

delivering a substantially constant current to the element;

measuring the voltage between the two measuring locations for determining the length of the fissure; and accomplishing the voltage measurement and the delivery of the current by means of separate conductors leading to the element.

6. The method as defined in claim 5, further including the steps of:

carrying out the infeed and removal of the current at two supply locations which are separated from the measuring locations.

7. The method as defined in claim 6, further including the steps of:

measuring the voltage drop at the element at a section of the current path between a supply location and the measuring location which is closer to and along the current path; and controlling and varying the measuring current in order to maintain essentially constant said voltage drop.

8. An apparatus for determining the time dependency of the length of a fissure in a test specimen during a fracture test, comprising:

a substantially flat electrically conductive element insulated at one face, means for securing said element to a surface of a test specimen;

said element having a measuring section of a size sufficient to completely cover the test specimen at the region of a fissure of the test specimen which forms during the fracture test;

said measuring section having two measuring locations;

said measuring section being compact and free of openings; and a measuring device for determining an electrical parameter between said two measuring locations.

9. The apparatus as defined in claim 8, wherein:

said measuring section is substantially symmetrical with respect to a plane of symmetry;

said measuring section having a notch which is substantially symmetrical with respect to said plane of symmetry and terminates in a tip located in said plane of symmetry; and said measuring locations are arranged in such a manner that the total measuring current flowing therebetween must travel over the element covering the region of the fissure.

10. The apparatus as defined in claim 8, further including:

conductors for connecting the measuring locations with the measuring device;

the measuring section having an outline which is configured, the conductors are connected with the measuring device and measuring locations such that the resistance of the measuring section linearly changes with the length of the fissure as it is being formed.

11. The apparartus as defined in claim 10, wherein:

the measuring section is substantially symmetrical with respect to a plane of symmetry;

said measuring section having a notch which is substantially symmetrical with respect to the plane of symmetry and terminates in a tip located in said plane of symmetry;

said measuring locations are arranged in such a manner that the total measuring current between said measuring locations must pass over the entire fissure length of the element covering the fissure;

said measuring section widening at least at a partial section merging with the notch and towards an edge of the measuring section which faces away from said notch.

12. The apparatus as defined in claim 8, wherein:

said measuring device contains a current source for producing a substantially constant measuring current;

said current source being connected by means of two conductors with said element;

said element having supply locations;

each of the conductors being connected with the element at a respective one of the supply locations;

the measuring device including means for voltage measurement;

said voltage measurement means being connected by two conductors with two measuring locations of the element;

said measuring locations being separated from said supply locations and arranged such that the current path from one of the supply locations extends past the one measuring location about the fissure and thereafter past the other measuring location to the other supply location.

13. The apparatus as defined in claim 12, wherein:

said element has an intermediate location between one of the supply locations and the measuring location which is located closer to the current path and extending along the current path;

a conductor for connecting said intermediate location with the measuring device;

said measuring device having means for measuring the voltage drop between the intermediate location and the measuring location or the supply location and for regulating the current in order to maintain said voltage drop at a constant value.

* * * * *